(12) United States Patent
Wohlman et al.

(10) Patent No.: US 6,545,052 B2
(45) Date of Patent: Apr. 8, 2003

(54) METHODS AND COMPOSITIONS FOR INHIBITING FREE RADICAL POLYMERIZATION IN SKIN AND HAIR

(75) Inventors: Alan Wohlman, Northbrook, IL (US); Anthony J. O'Lenick, Jr., Dacula, GA (US)

(73) Assignee: Fan Tech, Ltd., Chicago, IL (US)

( * ) Notice: Subject to any disclaimer, the term of this patent is extended or adjusted under 35 U.S.C. 154(b) by 0 days.

(21) Appl. No.: 09/725,560

(22) Filed: Nov. 29, 2000

(65) Prior Publication Data

US 2002/0094342 A1 Jul. 18, 2002

Related U.S. Application Data
(60) Provisional application No. 60/202,562, filed on May 10, 2000.

(51) Int. Cl.$^7$ .................. A01N 47/28; A01N 37/02; A61K 7/00; C07C 53/00; A23G 3/30
(52) U.S. Cl. .................. 514/587; 514/585; 514/580; 514/547; 424/401; 554/224; 426/3
(58) Field of Search .................. 426/3; 554/224; 424/401; 514/547, 580, 585, 587

(56) References Cited

U.S. PATENT DOCUMENTS

| | | | |
|---|---|---|---|
| 2,154,341 A | 4/1939 | Martin et al. .................. 37/16 |
| 2,662,096 A | 12/1953 | Huebner et al. .................. 260/552 |
| 3,483,296 A | 12/1969 | Martin et al. .................. 424/322 |
| 3,743,736 A | 7/1973 | Porter et al. .................. 424/267 |
| 3,852,348 A | 12/1974 | Teach .................. 260/553 |
| 3,991,008 A | 11/1976 | Temin et al. .................. 260/42.15 |
| 4,925,581 A | 5/1990 | Erickson et al. .................. 252/48.2 |
| 5,079,304 A | * 1/1992 | DeMarco .................. 525/329.8 |
| 5,262,072 A | 11/1993 | Camenzind et al. .................. 252/32.7 |
| 5,434,283 A | 7/1995 | Wang et al. .................. 554/224 |
| 5,441,984 A | 8/1995 | Heath et al. .................. 514/595 |
| 5,747,528 A | 5/1998 | Kakidas .................. 514/456 |
| 6,013,818 A | * 1/2000 | O'Lenick, Jr. .................. 554/224 |
| 6,136,330 A | * 10/2000 | Soliman et al. .................. 424/401 |
| 6,180,668 B1 | * 1/2001 | O'Lenick, Jr. et al. ..... 514/547 |

FOREIGN PATENT DOCUMENTS

| | | |
|---|---|---|
| DE | 208 298 A | 5/1984 |
| EP | 0 466 639 B1 | 1/1992 |
| EP | 0 903 349 A2 | 3/1999 |
| WO | WO 96/28008 | 9/1996 |

OTHER PUBLICATIONS

T.S. Chao et al. "Some Synergistic Antioxidants for Synthetic Lubricants," Symposium on Synthetic and Petroleum–Based Lubricants Presented Before the Division of Petroleum Chemistry, Inc., 27(2), 362–379, American Chemical Society, Las Vegas Meeting, Mar. 28–Apr. 2, 1982.

T.P. Abbott "Oxidative Stability System in Meadowfoam," Abstract from the 89$^{th}$ AOCS Annual Meeting & Expo, Chicago, Illinois, May 10–13 (1998).

M. Rechcigl, Jr. CRC Handbook of Naturally Occurring Food Toxicants, CRC Press, Inc. (Boca Raton, Florida), pp. 15–30 (1983).

S. Vaughn et al. "Isolation and Identification of (3–Methoxyphenyl) Acetonitrile as a Phytotoxin from Meadowfoam (*Limnanthes alba*) Seedmeal," Journal of Chemical Ecology, vol. 22, No. 10, 1939–1949 (1996).

T. Johns et al. "Anti–Reproductive and Other Medicinal Effects of *Tropaeolum Tuberosum*," Journal of Ethnopharmacology 5, 149–161 (1982).

T.A. Isbell et al. "Oxidative Stability Index of Vegetable Oils in Binary Mixtures with Meadowfoam Oil," Industrial Crops and Products 9, 115–123 (1999).

K. Tian et al. "Determination of Oxidative Stability of Oils and Fats," Anal. Chem. 71, 1692–1698 (1999).

S. El. Migirab et al. "Isothiocyanates, Thioureas et Thiocarbamates Isoles De Pentadip landra Brazzeana," Phytochemistry 16, 1719–1721 (1977).

W.W. Christie "Antioxidants," Bell & Bain Ltd., Glasgow, The Oily Press, Ltd. (Dundee, Scotland, 1988), pp. 133–159.

G. Kajimoto et al. "Changes in Organic Acid Formation in Volatile Degradation Products During Oxidation of Oils Treated with Antioxidant," Fac. Nutr., Kobe Gakuin Univ., Kobe, Japan. Nippon Eiyo, Shokuryo Gakkaishi 51(4), 207–212 (1998).

K. Ziegler–Skylakakis "S–Oxygenation of Thiourea Results in the Formation of Genotoxic Products," Environ. Mol. Mutagen. 31(4), 362–373 (1998).

S.L. Mali et al. "Phytochemical Oxidation of Phenyl–3–(2–Pyridly)Thiourea by Singlet Oxygen," Asian J. Chem. 5(4), 808–812 (1993).

A. Mustafa et al. "Reaction of Thiourea with Hydrogen Peroxide: Carbon–13 NMR Studies of an Oxidative/Reductive Bleaching Process," Text. Res. J. 62(2), 94–100 (1992).

Internet "Uses of Meadowfoam Seed Oil™," Mar. 9, 2000, [Online][Retrived From http://www.meadowfoam.com/uses/htm.].

(List continued on next page.)

*Primary Examiner*—Sreeni Padmanabhan
*Assistant Examiner*—Michael A. Willis
(74) *Attorney, Agent, or Firm*—Roberta L. Hastreiter; Scott B. Feder; Lord, Bissell & Brook

(57) ABSTRACT

A method is provided for inhibiting free radical degradation in the skin of a human or nonhuman animal comprising contacting the skin with a skin treatment composition having a concentration of a 1-(3-methoxybenzyl)-3-substituted thiourea compound effective for inhibiting free radical generation. Skin protecting compositions comprising a free radical inhibiting concentration of a 1-(3-methoxybenzyl)-3-substituted thiourea compound, and optionally a sunscreeen composition, are also provided.

21 Claims, No Drawings

OTHER PUBLICATIONS

T. Abbott et al. "Antioxidants from Meadowfoam Stabilizes Other Oils," Abstract, Assoc. for the Adv. of Ind. Crops, Oct, 15–17, 2000, St. Louis, MO.

89th Am. Oil Chem. Soc., May 10–13, 1998, Chicago, Illinois. This presentation discussed some of the compounds that are present in crude meadowfoam seed oil that do not contribute substantially to the oxidative stability of lipids or oils. It did not discuss any 1-(3-methoxybenzyl)-3-substituted thiourea compounds.

Assoc. for the Adv. of Ind. Crops, Oct. 15–17, 2000, St. Louis, MO. This presentation identified the presence of 1,3-di(3-methoxybenzyl) thiourea in meadowfoam seed oil. No other 1-(3-methoxybenzyl)-3-substituted thiourea compounds were discussed.

Martin G. Ettlinger et al. "The Mustard Oil of *Limnanthes douglasii* Seed, m–Methoxybenzyl Isothiocynate," Journal of the American Chemical Society, vol. 78, No. 9, pp. 1952–1954 (1956).

\* cited by examiner

METHODS AND COMPOSITIONS FOR INHIBITING FREE RADICAL POLYMERIZATION IN SKIN AND HAIR

This is a continuation-in-part of U.S. Provisional Application Ser. No. 60/202,562, filed May 10, 2000, which is incorporated herein by reference.

FIELD OF THE INVENTION

This invention relates to novel thiourea compounds for use in personal care product applications, such as skin care and hair care products, to protect the skin and hair from degradation caused by free radical polymerization and oxidation.

BACKGROUND OF THE INVENTION

Skin and hair are exposed to a variety of environmental factors that tend to degrade it. These include but are not limited to sun exposure, exposure to ozone, smog and other airborne pollutants. These conditions cause the skin to wrinkle, dry out, turn scaly and in extreme cases develop disease states like melanoma. Hair becomes brittle and dry and is cosmetically unappealing. The present invention relates to a new series of free radical inhibitors that protect the skin and hair from the deleterious effects of these environmental conditions.

The ultraviolet (UV) wavelengths of sunlight can cause sunburn (erythema) and blistering (edema). Exposure to ultraviolet light can also cause the skin to feel dry and taut in moderate doses, and to peel if exposed to higher doses. These acute, or short term, effects are readily perceptible and oftentimes uncomfortable and painful. While the exposure of the skin to the damaging effects of the sun can cause potential health problems, the exposure of hair to the sun can cause the hair to become dehydrated, weakened, and, in some instances, bleached. Hair that is damaged by sun exposure may become cosmetically unacceptable.

Human skin can be protected from some of these environmental effects. Moisturizers can readily reverse the appearance of dryness regardless of whether it results from low humidity conditions or UV light, and relieve the tautness of the skin caused by UV light exposure. These products either attract moisture from the environment to the skin's surface, or reduce the amount of evaporative loss from the surface of the skin. These products also add needed moisture to the skin from the formulation itself, and add a layer of emollients on the skin surface to leave it softer and more supple.

According to the free radical theory of premature aging of the skin, ultraviolet light can produce reactive oxygen species (ROS) that damage the skin. ROS are a collection of reactive free radicals produced from the oxygen molecule, and include singlet oxygen, the superoxide radical, hydrogen peroxide, and the hydroxyl radical, as well as the reaction products produced by these free radicals. Due to their reactivity, ROS relatively indiscriminately react with other molecules, and generate a cascade of harmful free radical reactions in the skin.

The skin possesses certain defense mechanisms against the generation of ROS. These defenses include the presence of enzymes such as superoxide dismutase, catalase, glutathione transferase, glutathione peroxidase and glutathione reductase, as well as antioxidants such as tocopherols, ubiquinone, ubiquinol, ascorbic acid and dehydroascorbic acid. Unfortunately, ultraviolet light entering the skin can easily overwhelm these defense systems, such that the amount of superoxide dismutase and glutathione transferase in the skin declines significantly upon irradiation with solar ultraviolet light. Simultaneous with the loss of these reducing enzymes, there is a dramatic increase in conjugated double bonds formed in the skin from the linoleates present in cell membranes. There is also an increase in thiobarbituric acid reactive substances present in the skin, which represent a collection of molecules that are formed from ROS.

Since sunscreens are unable to completely protect the skin against the adverse effects of ultraviolet radiation, alternative modes of protection have been proposed. Vitamins, such as Vitamin E acetate, have been shown to make the skin softer and smoother after topical application, which can offset some of the damaging effects of the sun. Vitamin A palmitate has been shown to create smoother skin and help enhance the process of cellular turnover. This enhancement rids the skin of the outermost dead layer of skin by bringing more youthful appearing skin cells to the surface. Other materials, such as hyaluronic acid and pyrrolidone carboxylic acid (PCA), have also been used for their ability to enhance the moisture binding capacity of the skin and therefore lead to smoother, softer skin.

Compositions that incorporate Vitamins A or E, or their derivatives, in sunscreen compositions, are shown in U.S. Pat. Nos. 4,454,112; 5,532,805; and 5,378,461. The use of Vitamin C in combination with Vitamins A, E, B and other agents in a skin protectant composition, is described in U.S. Pat. No. 4,938,960. An antioxidant preparation that is said to protect the skin against harmful ultraviolet radiation is disclosed in U.S. Pat. No. 5,607,921, and contains Vitamin C, in combination with Vitamins A and E, and monosaccharide or amide precursors. Sunscreen compositions containing panthenol and other agents are disclosed in U.S. Pat. Nos. RE 33,845; 5,505,935; 5,445,823; and 5,573,754. The antioxidant effect of superoxide dismutase when externally applied to the skin to protect against the effects of ultraviolet radiation is also described in U.S. Pat. No. 5,601,806.

In spite of advances in recent years in the protection of skin from harmful ultraviolet radiation, the epidemic of skin cancer and skin damage from the effects of this radiation has continued unabated. The loss of portions of the ozone layer from environmental pollution is believed to have contributed to an increase in ambient ultraviolet radiation that reaches exposed skin. There is a significant need for commercially acceptable or improved preparations that can be topically applied expecially to human and animal skin, to offset the harmful effects of ultraviolet radiation.

SUMMARY OF THE INVENTION

The present invention relates to the discovery that certain 1-(3-methoxybenzyl)-3-substituted thiourea compounds and compositions containing same, when applied topically to the skin or hair of a human or nonhuman animal, inhibit free radical degradation (i.e., degradation caused by free radical polymerization of natural compounds present in skin tissue or hair), and oxidation of the skin or hair. The 1-(3-methoxybenzyl)-3-substituted thiourea compounds are soluble in oils and alcohols and the like, and may desirably be provided in an oil based composition, or in the oil phase of an emulsion, which can be applied to the skin or hair.

The present invention thus entails a method for protecting skin or hair from free radical polymerization and degradation, which comprises contacting the skin or hair with a concentration of a 1-(3-methoxybenzyl)-3-substituted thiourea compound of formula I which is effective to inhibit free radical polymerization,

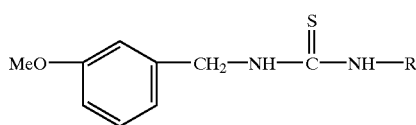

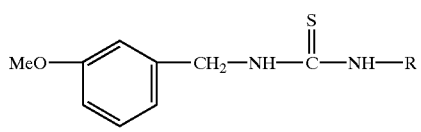

wherein R is a $C_1$–$C_{20}$ linear or branched alkyl such as methyl, ethyl, propyl, isopropyl, butyl, isobutyl, tert-butyl, pentyl, hexyl, octyl, decyl, nonyl, dodecyl, and the like, $C_5$–$C_7$ cycloalkyl, such as cyclopentyl, cyclohexyl or cycloheptyl and the like, $C_6$–$C_7$ aryl such as phenyl or benzyl and the like, hydroxy- or alkoxy-substituted $C_6$–$C_7$ aryl such as hydroxyphenyl, methoxyphenyl, ethoxyphenyl, hydroxybenzyl, methoxybenzyl or ethoxybenzyl. Among compounds of the formula I, a presently preferred free radical inhibiting compound is 1,3-di(3-methoxybenzyl) thiourea, i.e., a compound of formula I wherein R is a 3-methoxybenzyl moiety. The compound, 1,3-di(3-methoxybenzyl) thiourea, has been identified as an antioxidant in meadowfoam seed oil as disclosed in U.S. Provisional Patent Application No. 60/202562, filed May 10, 2000, which is incorporated herein by this reference.

The present invention also provides skin treatment compositions comprising between about 0.01 wt. % and about 5 wt. %, preferably between about 0.1 wt. % and about 2 wt. %, of a free radical inhibiting compound of formula I in an appropriate base composition such as a moisturizing composition, skin lotion, sunscreen lotion, sunblock lotion, or the like. Hair treatment compositions are also provided which comprise between about 0.01 wt. % and about 5 wt. %, preferably between about 0.1 wt. % and about 2 wt. %, of a free radical inhibiting compound of formula I in an appropriate base composition such as a hairspray, gel, mousse or the like. As used herein, the term "base composition" includes cosmetic base compositions for skin and base compositions for hair which may be conventionally provided as oils, oil-in-water emulsions, water-in-oil emulsions, oil-in-water-in-oil (O/W/O) emulsions, microemulsions, gels or the like.

Presently preferred compounds of formula I for use in accordance with the present inventions are 1,3-di(3-methoxybenzyl) thiourea; 1-(3-methoxybenzyl)-3-ethyl-2-thiourea; 1-(3-methoxybenzyl)-3-propyl-2-thiourea; 1-(3-methoxybenzyl)-3-hexyl-2-thiourea; 1-(3-methoxybenzyl)-3-dodecyl-2-thiourea; 1-(3-methoxybenzyl)-3-(4-hydroxyphenyl)-2-thiourea; and 1-(3-methoxybenzyl)-3-(3-methoxyphenyl)-2-thiourea. The free radical inhibiting activity of the compounds of formula I diminish the deleterious effects of environmental factors when applied to the skin alone, or desirably in combination with one or more sunscreen compositions. 1,3-di(3-methoxybenzyl) thiourea is a particularly preferred free radical inhibitor compound. Meadowfoam seed oil may be used as an ingredient in emulsion or the like to provide an effective free radical inhibitor concentration of 1,3 di(3-methoxybenzyl) thiourea.

DETAILED DESCRIPTION OF THE INVENTION

In one of its aspects, the present invention entails a method of protecting the skin or hair of a human or nonhuman animal from free radical degradation comprising contacting the skin or hair with an amount of a 1-(3-methoxybenzyl)-3-substituted thiourea compound of the formula I in a concentration which is sufficient to inhibit free radical degradation wherein R is selected from the group consisting of $C_1$–$C_{20}$ linear or branched alkyl; $C_5$–$C_7$ cycloalkyl; alkoxy-substituted $C_5$–$C_7$ cycloalkyl; hydroxy-substituted $C_5$–$C_7$ cycloalkyl; $C_6$–$C_7$ aryl; hydroxy-substituted $C_6$–$C_7$ aryl; and alkoxy-substituted $C_6$–$C_7$ aryl. In a particularly preferred embodiment, the substituted aryl moiety is a 3-hydroxy-substituted or 3-alkoxy-substituted aryl compound.

In another of its aspects, the present invention entails a skin treatment composition or hair treatment composition capable of inhibiting free radical degradation of the skin or hair, which comprises a skin cosmetic base composition or hair cosmetic base composition, which contains a concentration of a 1-(3-methoxybenzyl)-3-substituted thiourea compound of the formula I

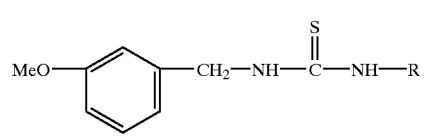

which is effective to inhibit free radical degradation of the skin or hair, wherein R is selected from the group consisting of $C_1$–$C_2$ linear or branched alkyl; $C_5$–$C_7$ cycloalkyl; hydroxy- or alkoxy-substituted $C_5$–$C_7$ cycloalkyl; $C_6$–$C_7$ aryl; and hydroxy- or alkoxy-substituted $C_6$–$C_7$ aryl. The skin or hair treatment composition of the invention may optionally be supplemented with one or more conventional sunscreen compositions, vitamins, or other compounds useful for protecting skin or hair from the degradative effects of ultraviolet radiation. The novel thiourea derivatives according to formula I are described in U.S. Provisional Patent Application No. 60/202562, filed May 10, 2000, which is incorporated herein by this reference.

As used herein, "$C_1$–$C_{20}$ linear or branched alkyl" shall include methyl, ethyl, propyl, isopropyl, butyl, isobutyl, t-butyl, pentyl, 2-methyl-pentyl, 3-methyl-penyl, hexyl, octyl, decyl, dodecyl, and the like. The term "$C_5$–$C_7$ cycloalkyl" shall include cyclopentyl, cyclohexyl and cycloheptyl. The term "hydroxy- or alkoxy-substituted $C_5$–$C_7$ cycloalkyl" shall include cyclopentyl, cyclohexyl and cycloheptyl moieties that are substituted with an hydroxy, methoxy, ethoxy, or propoxy group or the like. The term "$C_6$–$C_7$ aryl" shall include phenyl and benzyl. The term "hydroxy- or alkoxy-substituted $C_6$–$C_7$ aryl" shall include phenyl and benzyl moieties that are substituted with an hydroxy, methoxy, ethoxy, or propoxy group or the like.

Compounds of the formula I may be synthesized by reacting 3-methoxybenzylamine and an appropriately selected isothiocyanate compound of the formula II S=C=N—R, wherein R is defined the same as for compounds of formula I. The reaction may be carried out by slowly adding the isothiocyanate to an aqueous solution of 3-methoxybenzylamine, preferably under a nitrogen atmosphere. The thiourea product of the reaction, which is a compound of formula I, may be recovered and purified by mixing the reaction products with a solvent that is not miscible with water but one that is a solvent for the thiourea, such as methylene chloride, chloroform, toluene or diethyl ether. The water layer may or may not be acidified to enhance separation and recovery of the thiourea compound of the invention. The thiourea, dissolved in the solvent layer can be drawn off from the water layer, dried and the resulting crude thiourea purified by recrystallization in an appropriate solvent such as ethanol. See, Example 1. See also, generally, the procedure of Moore and Crossley, Organic Synthesis 2, 617–618 (note 4).

The reactants, 3-methoxybenzylamine and an appropriate isothiocyanate compound as defined above, may be obtained commercially or synthesized by routine methods known in the art, and the resultant product compounds of formula I may be readily isolated by routine methods well-known to those having ordinary skill in the art. Suitable isothiocyanate reactants for synthesizing compounds of the present invention may be obtained as well-known in the art from degradation of glucosinolates present in seed oils and other lipids. In an aqueous solution containing the enzyme thioglucosidase, glucosinolate compounds are degraded into isothiocyanates and other degradation products. See, Vaughn, et al., J. Chem. Ecol. 22, 1939–49 (1996); and C. VanEtten and H. Tookey, (1983) Glucosinolates, pp. 15–30 in M. Rechcigl (ed.) "Naturally Occurring Food Toxicants," CRC Press, Boca Raton, Fla. The isothiocyanate fraction of the glucosinolate breakdown products thus may be isolated and reacted with 3-methoxybenzylamine as described above to provide compounds of the present invention. Approximately 100 glucosinolate compounds have been identified in plants from 11 different plant families including mustard, rapeseed, cabbage, garlic mustard and crambe (S.F. Vaughn, 1999. Glucosinolates as Natural Pesticides in Biologically Active Natural Products: Agrochemicals, H. G. Cutler and S. J. Cutler, Eds, CRC Press, Boac Raton, Fla.) Oils isolated from glucosinolate containing plants are normally deodorized by steam sparging to remove volatile compounds which includes isothiocyanates and amines. Thus, a variety of isothiocyanate compounds and benzylamine compounds may be obtained from the waste distillation product generated in the process of purifying such oils and employed as reactants in synthesizing compounds of the present invention.

3-methoxybenzylamine may be purchased commercially or may be isolated from meadowfoam seed oil by extraction into an immiscible acidified aqueous layer which is separated from the oil, washed with a nonpolar solvent, treated with a base to lower pH, and the amine extracted into an immiscible solvent. The 3-methoxybenzylamine compound may be further purified by crystallization from ethanol or similar solvent and/or purified by reverse-phase HPLC using a $C_{18}$ column, eluting with a gradient starting at 100% methanol and proceeding to about 80% methanol:20% chloroform. The peak containing 3-methoxybenzylamine may be identified by its retention time on the HPLC column in comparison to the retention time for a known standard sample of 3-methoxybenzylamine. Other natural amines may be purchased commercially or may be similarly extracted from natural sources and purified with reference to known standard samples and/or identified by standard chemical methods for identification of amines (e.g., chromatography, infrared spectroscopy, mass spectroscopy, elemental analysis, nuclear magnetic resonance analysis and the like).

The phrase "an effective concentration of a free radical inhibitor" or "concentration which is effective to inhibit free radical degradation" as used herein means a concentration of a free radical inhibitor compound that is capable of reducing the amount of free radical polymerization of a polymerizable compound as compared to the amount of free radical polymerization obtained in the absence of the free radical inhibitor compound. Methods of determining the ability of a compound to inhibit a free radical polymerization reaction are well known in the art.

A presently preferred method for determining the free radical inhibitory capacity of a compound is based on the ability of such a compound to inhibit free radical polymerization of acrylic acid to polyacrylic acid. A suitable assay for demonstrating an effective concentration of a selected free radical inhibitor compound is an assay which determines the ability of such a compound to inhibit the polymerization of a 30% aqueous solution of acrylic acid at 85° C. after initiation with 0.1% azobisisobutyrylnitrile. The inhibitory capacity of such a compound is determined by comparing the percent of polyacrylic acid formed in the presence and absence of a predetermined concentration of the selected free radical inhibitor compound, with inhibition being demonstrated by a detectable decrease in the amount of polyacrylic acid formed in the reaction mixture containing the inhibitor as compared to the amount of polyacrylic acid formed in the reaction mixture to which an inhibitor was not added. As will be appreciated, the amount of polyacrylic acid formed is inversely related to the amount of acrylic acid (i.e., monomer) remaining in the reaction mixture at the end of the assay. The amount of acrylic acid may be routinely determined by measuring the iodine value of the reaction mixture or by other methods known in the art for determinating unsaturation. A well-known free radical inhibitor compound such as hydroquinone mono methyl ether (HQMME) may be used as a standard inhibitor compound in the assay.

The compounds of formula I herein are potent inhibitors of free radical polymerization, as well as scavengers of hydroperoxides which are known precursors to free radicals. The compounds of formula I also desirably absorb UV radiation at a wavelength of 280 nm. Due to their ability to inhibit free radical degradation, the compounds of formula I are capable of imparting free radical inhibition activity to the skin or hair in accordance with the methods of the present invention. Free radical degradation can be initiated and propogated even in the presence of an effective sunscreen composition. Thus, in one embodiment of the present invention, skin care compositions contain an effective concentration of a compound of formula I sufficient to inhibit free radical degradation, as well as an effective concentration of a sunscreen composition for absorbing UV light. The free radical inhibitor compounds of formula I and the sunscreen compounds have activities that are complementary to one another. Among the well known sunscreen compositions (and the preferred percentages (w/w) that provide effective sunscreen protection), which may be used in accordance with the present invention, are UVA absorbers, including oxybenzone (2–6%), sulisobenzone (5–10%), dioxybenzone (3%), methyl anthranilate (3.5–5%), UVB absorbers, including aminobenzoic acid (5–15%), amyldimethyl PABA (1–5%), 2-ethoxyethyl p-methoxycinnamate (1–3%), diethanolamine p-methoxycinnamate (8–10%), digalloyl trioleate (2–5%), ethyl 4-bis(hydroxypropyl) aminobenzoate (1–5%), 2-ethylhexyl-2-cyano-3,3-diphenylacrylate (7–10%), ethylhexyl p-methoxycinnamate (2–7.5%), 2-ethylhexyl salicylate (3–5%), glyceryl aminobenzoate (2–3%), homomenthyl salicylate (4–15%), lawsone with dihydroxyacetone (0.25% with 33%), octyldimethyl PABA (1.4–8%), 2-phenylbenzimidazole-5-sulfonic acid (1–4%), triethanolamine salicylate (5–12%), and the physical UV absorbers, red patrolatum (30–100%) and titanium dioxide (2–25%).

The free radical inhibiting compounds, alone or in combination with a suitable suncreen compound, may be included into a variety of skin care or hair care compositions. It is presently contemplated that the free radical inhibitor compounds of formula I will be dissolved in an oil, lipid or alcohol which is used to prepare a skin treatment composition or a hair treatment composition of the invention. Suitable base compositions for preparing the skin or hair treatment compositions of the invention include lotions, liquids, creams, ointments, and the like, which may be conventionally provided as oils, oil-in-water emulsions, water-in-oil emulsions, oil-in-water-in-oil emulsions, microemulsions, liposomes or the like as are well known in the art. Various compositions useful for skin treatment or for hair treatment, which can be used (with or without the sunscreen compositions being added) to deliver compounds of formula I to the skin or hair may be prepared from the disclosures in for example, U.S. Pat. Nos. 4,115,547; 4,172,122; 4,454,112; 4,567,038; 4,592,906; 4,663,157; 4,847,267; 4,938,960 and 5,980,871. The Examples that follow provide skin treatment compositions of the invention including free radical inhibitor compounds of the formula I.

The following nonlimiting examples are illustrative of the invention.

EXAMPLE 1

This example demonstrates the synthesis of 1,3-di-(3-methoxybenzyl) thiourea. To a three neck, 100-ml flask fitted with a condenser, a rubber syringe septum and a nitrogen inlet was added 20-ml water and 3.6 g (25.8 mmol) of 3-methoxybenzyl amine. The reaction vessel was purged with nitrogen and stirred with a Teflon-coated magnetic stir bar. 3-methoxybenzyl isothiocyanate 2.59 ml (3.0 g, 16.7 mmol) was then added dropwise (approx. 1 drop/5–10 sec) from a glass syringe. A separate layer forms and the mixture was stirred for 1 additional hour at room temperature. The water layer was acidified with 1 M HCl (about 10 ml) to pH 5.5. Methylene chloride, (15 ml) was then added and the two layers transferred to a separator funnel. The lower layer (methylene chloride) was removed. The water layer was washed with methylene chloride twice more with 10 ml of methylene chloride. The methylene chloride layers were combined and washed with 0.1 M HCl and then water. The methylene chloride solution was dried over 3A molecular sieves and then evaporated to dryness in a rotating solvent evaporator. The resulting viscous liquid was taken up in 20 ml ethanol that had been heated to 35° C. and the product recrystallized by cooling in a refrigerator twice from ethanol as white crystals, dried in vacuum at room temperature and weighed. A second recrystallization was made from the mother liquor to retrieve additional product for a yield of 79.8% in the first crystal batch and 83.2% for the combined batches of crystals. Analysis of the product by NMR, mass spectroscopy and elemental analysis revealed the product to be 1,3-di-(3methoxybenzyl) thiourea.

EXAMPLE 2

The method described in example 1 is repeated except that 0.8 grams of methylamine is substituted for the 3-methoxybenzylamine.

EXAMPLE 3

The method described in example 1 is repeated except that 1.1 grams of ethylamine is substituted for the 3-methoxybenzylamine.

EXAMPLE 4

The method described in example 1 is repeated except that 2.6 grams of hexylamine is substituted for the 3-methoxybenzylamine.

EXAMPLE 5

The method described in example 1 is repeated except that 4.1 grams of decylamine is substituted for the 3-methoxybenzylamine.

EXAMPLE 6

The method described in example 1 is repeated except that 4.8 grams of dodecylamine is substituted for the 3-methoxybenzylamine.

EXAMPLE 7

The method described in example 1 is repeated except that 5.5 grams of $CH_3(CH_2)_{13}NH_2$ is substituted for the 3-methoxybenzylamine.

EXAMPLE 8

The method described in example 1 is repeated except that 6.9 grams of $CH_3(CH_2)_{17}NH_2$ is substituted for the 3-methoxybenzylamine.

EXAMPLE 9

The method described in example 1 is repeated except that 7.7 grams of $CH_3(CH_2)_{19}NH_2$ is substituted for the 3-methoxybenzylamine

EXAMPLE 10

This example demonstrates the free radical inhibitor activity of 1,3-di(3-methoxybenzyl)thiourea. Into each of three 250 ml beakers, labeled "1," "2," and "3" respectively, is added 200 ml of a 30% solution of acrylic acid (in water). One-tenth gram of 1,3-di(3-methoxybenzyl)thiourea was dissolved in 9.9 grams of isopropyl alcohol to give a 1% (w/w) solution of the free radical inhibitor compound. One-tenth gram of the known free radical inhibitor hydroquinone mono methyl ether was dissolved in 9.9 grams isopropyl alcohol to give a 1% solution to be used as a positive control to demonstrate that the assay is capable of detecting inhibition of free radical polymerization. One-tenth gram of azobisisobutyronitrile (a free radical initiator) was dissolved in 9.9 grams of isopropyl alcohol to provide a 1% solution of the free radical initiator. To beaker 1, containing 200 ml of the acrylic acid solution was added 0.6 ml of the 1% solution of 1,3-di(3-methoxybenzyl)thiourea. To beaker 2, containing 200 ml of the acrylic acid solution was added 0.6 ml of the 1% solution of hydroquinone mono methyl ether. To beaker 3 was added 0.6 ml of isopropyl alcohol (no inhibitor). Beakers 1, 2 and 3 containing the acrylic acid solution, with or without inhibitor compound added thereto, were heated to 85° C. on a hot plate and 0.2 ml of the 0.1% solution of azobisisobutyrlnitrile was then added to each beaker to initiate the free radical polymerization reaction. After 3 hours, the beakers were removed from the hot plate to stop the reaction from progressing further, and the amount of acrylic acid which remained in the reaction mixture was determined by measuring the iodine value of an aliquot of the reaction mixture using the A.O.C.S. Method Tg 1a-64T in *Official Methods And Recommended Practices Of The AOCS*, by American Oil Chemists' Society, Champaign, Ill. The results showed that the free radical polymerization reaction was strongly inhibited by 1,3-di(3-methoxybenzyl)thiourea.

| Beaker No. | Inhibitor Compound | % Polymerization (after 3 hours at 85° C.) |
|---|---|---|
| 1 | 1,3-di(3-methoxybenzyl)thiourea | 48.6% |
| 2 | hydroquinone mono methyl ether | 78.6% |
| 3 | Control (no inhibitor) | 84.8% |

EXAMPLE 11

The free radical inhibition assay described in Example 10 is carried out as described except that the 1-(3-methoxybenzyl)-3-substituted thiourea compounds of Examples 2–9 are separately tested, and the results show that the compounds of Examples 2–9 are effective inhibitors of free radical polymerization.

EXAMPLE 12

A skin treatment composition containing 1,3 di-(3-methoxybenzyl)thiourea as the free radical inhibitor is prepared by blending 66 grams of mineral oil (B.P.) with 2.0 grams of 1,3-di-(3-methoxybenzyl) thiourea, 3.0 grams of 2-ethylhexyl palmitate, 27.0 grams of isopropyl myristate and an effective amount of a suitable fragrance.

EXAMPLE 13

A skin treatment composition containing 1,3 di-(3-methoxybenzyl)thiourea as the free radical inhibitor is prepared by blending 66 grams of meadowfoam seed oil, 3.0-grams of 2-ethylhexyl palmitate, 27.0 grams of isopropyl myristate and an effective amount of a suitable fragrance.

EXAMPLE 14

Example 13 is repeated except that the meadowfoam seed oil is supplemented with 1.0 gram of exogenously added 1,3 di-(3-methoxybenzyl)thiourea that is conventionally blended into the meadowfoam seed oil prior to preparing the skin treatment composition.

EXAMPLE 15

A skin treatment composition containing a free radical inhibitor and a sunscreen compound (homosalate) is prepared from Preparation A and Preparation B as follows.

| Preparation A | | Preparation B | |
|---|---|---|---|
| Lanolin | 5.00 g | Methylparaben | 0.10 g |
| Homosalate | 8.00 g | Edetate Disodium | 0.05 g |
| White Petrolatum | 2.50 g | Propylene Glycol | 5.00 g |
| Stearic Acid | 4.00 g | Triethanolamine | 1.00 g |
| Propylparaben | 0.50 g | Purified Water U.S.P. | 74.30 G |
| 1,3-di (3-methoxybenzyl) thiourea | 2.00 g | | |

Preparation A and Preparation B are heated separately to 77 to 82° C. with constant stirring until the content of each are solubilized. Then Preparation A is added slowly to Preparation B with constant stirring. Stirring is continued at room temperature (15 to 30° C.) until the emulsion formed is cooled to room temperature. Purified water is added to obtain 100 gram of the skin treatment composition.

The present invention has been described herein with some specificity and with reference to certain preferred embodiments thereof. Those persons having ordinary skill in the art will appreciate variations, modifications and substitutions which may be made to what has been described without departing from the scope and spirit of the invention which is defined by the following claims. The publications, technical specifications and patents which have been cited herein are hereby incorporated into this document by this reference.

We claim:

1. A method for inhibiting free radical degradation of skin or hair of a human or nonhuman animal comprising contacting the skin or hair with a composition comprising at least one 1-(3-methoxybenzyl)-3-substituted thiourea compound of formula I:

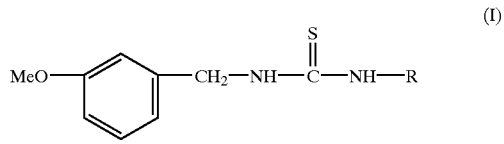

in a concentration which is effective to inhibit free radical polymerization, wherein R is selected from the group consisting of $C_1$–$C_{20}$ linear or branched alkyl; $C_5$–$C_7$ cycloalkyl; alkoxy-substituted $C_5$–$C_7$ cycloalkyl; hydroxy-substituted $C_5$–$C_7$ cycloalkyl; $C_6$–$C_7$ aryl; hydroxy-substituted $C_6$–$C_7$ aryl; and alkoxy-substituted $C_6$–$C_7$ aryl.

2. A method according to claim 1 wherein the composition comprises between about 0.01% and 5% by weight of the compound of formula I.

3. A method according to claim 2 wherein the composition comprises between about 0.1% and 2% by weight of the compound of formula I.

4. A method according to claim 1 wherein the compound of formula I is contained in an oil.

5. A method according to claim 4 wherein the composition is an emulsion.

6. A method according to claim 4 wherein the oil is meadowfoam seed oil.

7. A method according to claim 1 wherein R is selected from the group consisting of (i) $C_1$–$C_{20}$ linear alkyl, (ii) hydroxy-substituted $C_6$–$C_7$ aryl and (iii) alkoxy-substituted $C_6$–$C_7$ aryl moieties.

8. A method according to claim 1 wherein the compound of formula I is selected from the group consisting of 1,3-di (3-methoxybenzyl) thiourea; 1-(3-methoxybenzyl)-3-ethyl-2-thiourea; 1-(3-methoxybenzyl)-3-propyl-2-thiourea; 1-(3-methoxybenzyl)-3-hexyl-2-thiourea; 1-(3-methoxybenzyl)-3-dodecyl-2-thiourea; 1-(3-methoxybenzyl)-3-(4-hydroxyphenyl)-2-thiourea; and 1-(3-methoxybenzyl)-3-(3-methoxyphenyl)-2-thiourea.

9. A method according to claim 1 wherein the compound of formula I is 1,3-di(3-methoxybenzyl) thiourea.

10. A method according to claim 1 wherein the composition inhibits the free radical degradation of the skin after contacting the composition with the skin.

11. A method according to claim 1 wherein the composition inhibits the free radical degradation of the hair after contacting the composition with the hair.

12. A composition comprising a base composition and at least one 1-(3-methoxybenzyl)-3-substituted thiourea compound of formula I:

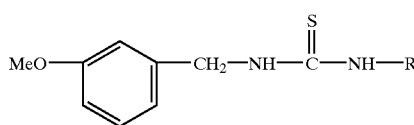

wherein R is selected from the group consisting of $C_1$–$C_{20}$ linear or branched alkyl; $C_5$–$C_7$ cycloalkyl; alkoxy-substituted $C_5$–$C_7$ cycloalkyl; hydroxy-substituted $C_5$–$C_7$ cycloalkyl; $C_6$–$C_7$ aryl; hydroxy-substituted $C_6$–$C_7$ aryl; and alkoxy-substituted $C_6$–$C_7$ aryl, wherein the compound of formula I is present in the composition in an amount effective to inhibit free radical polymerization, wherein the composition inhibits free radical degradation of skin or hair of a human or nonhuman animal after contacting the skin or hair with the composition, wherein the base composition comprises an oil that contains the compound of formula I and wherein the oil is meadowfoam seed oil.

13. A composition comprising a base composition and at least one 1-(3-methoxybenzyl)-3-substituted thiourea compound of formula I:

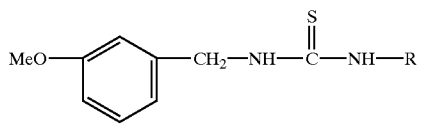

wherein R is selected from the group consisting of (i) $C_1$–$C_{20}$ linear alkyl, (ii) hydroxy-substituted $C_6$–$C_7$ aryl and (iii) alkoxy-substituted $C_6$–$C_7$ aryl, wherein the compound of formula I is present in the composition in an amount effective to inhibit free radical polymerization, and wherein the composition inhibits free radical degradation of skin or hair of a human or nonhuman animal after contacting the skin or hair with the composition.

14. A composition comprising a base composition and at least one 1-(3-methoxybenzyl)-3-substituted thiourea compound of formula I:

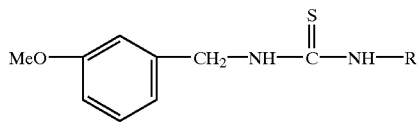

wherein R is selected from the group consisting of $C_1$–$C_{20}$ linear or branched alkyl; $C_5$–$C_7$ cycloalkyl; alkoxy-substituted $C_5$–$C_7$ cycloalkyl; hydroxy-substituted $C_5$–$C_7$ cycloalkyl; $C_6$–$C_7$ aryl; hydroxy-substituted $C_6$–$C_7$ aryl; and alkoxy-substituted $C_6$–$C_7$ aryl, wherein the compound of formula I is selected from the group consisting of 1,3-di(3-methoxybenzyl) thiourea; 1-(3-methoxybenzyl)-3-ethyl-2-thiourea 1-(3-methoxybenzyl)-3-propyl-2-thiourea; 1-(3-methoxybenzyl)-3-hexyl-2-thiourea; 1-(3-methoxybenzyl)-3-dodecyl-2-thiourea; 1-(3-methoxybenzyl)-3-(4-hydroxyphenyl)2-thiourea; and 1-(3-methoxybenzyl)-3-(3-methoxyphenyl)-2-thiourea, wherein the compound of formula I is present in the composition in an amount effective to inhibit free radical polymerization, and wherein the composition inhibits free radical degradation of skin or hair of a human or nonhuman animal after contacting the skin or hair with the composition.

15. A composition comprising a base composition and at least one 1-(3-methoxybenzyl)-3-substituted thiourea compound of formula I:

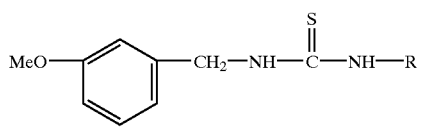

wherein R is selected from the group consisting of $C_1$–$C_{20}$ linear or branched alkyl; $C_5$–$C_7$ cycloalkyl; alkoxy-substituted $C_5$–$C_7$ cycloalkyl; hydroxy-substituted $C_5$–$C_7$ cycloalkyl; $C_6$–$C_7$ aryl; hydroxy-substituted $C_6$–$C_7$ aryl; and alkoxy-substituted $C_6$–$C_7$ aryl, wherein the compound of formula I is present in the composition in an amount effective to inhibit free radical polymerization, wherein the composition inhibits free radical degradation of skin or hair of a human or nonhuman animal after contacting the skin or hair with the composition, and wherein the composition further comprises a sunscreen compound in a concentration effective for sunscreen protection.

16. A composition comprising a base composition and at least one 1-(3-methoxybenzyl)-3-substituted thiourea compound of formula I:

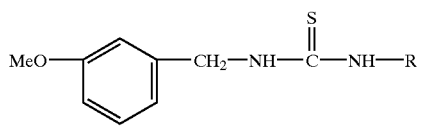

wherein R is selected from the group consisting of $C_1$–$C_{20}$ linear or branched alkyl; $C_5$–$C_7$ cycloalkyl; alkoxy-substituted $C_5$–$C_7$ cycloalkyl; hydroxy-substituted $C_5$–$C_7$ cycloalkyl; $C_6$–$C_7$ aryl; hydroxy-substituted $C_6$–$C_7$ aryl; and alkoxy-substituted $C_6$–$C_7$ aryl, wherein the compound of formula I is present in the composition in an amount effective to inhibit free radical polymerization, wherein the composition inhibits free radical degradation of skin or hair of a human or nonhuman animal after contacting the skin or hair with the composition and wherein the compound of formula I is 1,3-di(3-methoxybenzyl) thiourea.

17. A composition according to claim 15 wherein the base composition comprises an oil that contains the compound of formula I.

18. A composition according to claim 17 wherein the composition is an emulsion.

19. A composition according to claim 17 wherein the oil is meadowfoam seed oil.

20. A composition according to claim 14 which further comprises a sunscreen compound in a concentration effective for sunscreen protection.

21. A method for inhibiting free radical degradation of skin or hair of a human or nonhuman animal comprising contacting the skin or hair with a composition comprising at least one 1-(3-methoxybenzyl)-3-substituted thiourea compound of formula I:

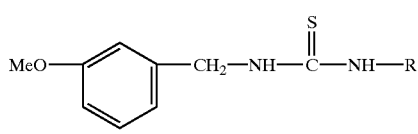 (I)

in a concentration which is effective to inhibit free radical polymerization, wherein R is selected from the group consisting of $C_1$–$C_{20}$ linear or branched alkyl; $C_5$–$C_7$ cycloalkyl; alkoxy-substituted $C_5$–$C_7$ cycloalkyl; hydroxy-substituted $C_5$–$C_7$ cycloalkyl; $C_6$–$C_7$ aryl; hydroxy-substituted $C_6$–$C_7$ aryl; and alkoxy-substituted $C_6$–$C_7$ aryl, with the proviso that, if the composition contains an oil in which a compound of formula I is naturally occurring in an amount effective to inhibit free radical polymerization, the composition further comprises an additional amount of a compound of formula I which is effective to inhibit free radical polymerization, which additional amount is exogenous to the naturally-occurring amount.

* * * * *